(12) United States Patent
Erikawa (10) Patent No.: US 9,364,645 B2
(45) Date of Patent: Jun. 14, 2016

(54) BALLOON CATHETER

(71) Applicant: TERUMO KABUSHIKI KAISHA, Shibuya-ku (JP)

(72) Inventor: Yutaka Erikawa, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/488,981

(22) Filed: Sep. 17, 2014

(65) Prior Publication Data

US 2015/0005803 A1 Jan. 1, 2015

Related U.S. Application Data (63) Continuation of application No. PCT/JP2012/080750, filed on Nov. 28, 2012.

(30) Foreign Application Priority Data

Mar. 23, 2012 (JP) ................................. 2012-068126

(51) Int. Cl.
*A61M 25/10* (2013.01)
*A61M 25/00* (2006.01)
*A61M 25/01* (2006.01)

(52) U.S. Cl.
CPC ........... *A61M 25/104* (2013.01); *A61M 25/005* (2013.01); *A61M 25/0052* (2013.01); *A61M 2025/0059* (2013.01); *A61M 2025/0183* (2013.01); *A61M 2025/109* (2013.01)

(58) Field of Classification Search
CPC ............ A61M 25/104; A61M 25/005; A61M 2025/0059; A61M 2025/109; A61M 25/0052; A61M 2025/0183; A61M 25/0029; A61M 2025/018; A61M 25/0136; A61M 2025/0161
USPC ..................................................... 604/103.04
See application file for complete search history.

(56) References Cited

U.S. PATENT DOCUMENTS 6,066,114 A * 5/2000 Goodin ............... A61M 25/104
604/103.04
6,589,207 B1 7/2003 El-Nounou
(Continued)

FOREIGN PATENT DOCUMENTS

JP 2001-95924 A 4/2001
JP 2001-333984 A 12/2001
(Continued)

OTHER PUBLICATIONS

International Search Report (PCT/ISA/210) mailed on Jan. 29, 2013, by the Japanese Patent Office as the International Searching Authority for International Application No. PCT/JP2012/080750.
The extended European Search Report issued on Oct. 13, 2015, by the European Patent Office in corresponding European Patent Application No. 12871924.21506 (4 pgs).

*Primary Examiner* — Theodore Stigell
(74) *Attorney, Agent, or Firm* — Buchanan Ingersoll & Rooney PC (57) ABSTRACT

A balloon catheter includes a proximal shaft, a distal shaft, an intermediate shaft positioned between the proximal shaft and the distal shaft, lumens that penetrate through the proximal shaft, the intermediate shaft, and the distal shaft and introduce and discharge a dilation fluid for a balloon, an inner tube shaft having a guide wire opening arranged at a boundary between the intermediate shaft and the distal shaft and through which the lumen extends, and a reinforcement member arranged in the lumen so as to suppress an occurrence of a kink. The reinforcement member has a tapered proximal portion fixed to the proximal shaft and arranged inside the lumen positioned in the intermediate shaft, a tapered distal portion arranged inside the lumen positioned in the distal shaft, and a straight transition portion positioned between the proximal portion and the distal portion. The transition portion is aligned with the guide wire opening.

17 Claims, 6 Drawing Sheets

(56) References Cited

U.S. PATENT DOCUMENTS 7,367,967 B2 * 5/2008 Eidenschink ..... A61M 25/0032
 604/523
2012/0004606 A1 1/2012 Lentz
2012/0303054 A1 * 11/2012 Wilson .............. A61M 25/0009
 606/194

FOREIGN PATENT DOCUMENTS

| JP | 2002-126085 A | 5/2002 |
| JP | 2003-517901 A | 6/2003 |
| WO | WO 01/45788 A1 | 6/2001 |
| WO | 2010/102105 A1 | 9/2010 |

* cited by examiner

BALLOON CATHETER

CROSS-REFERENCES TO RELATED APPLICATIONS

This application is a continuation of International Application No. PCT/JP2012/080750 filed on Nov. 28, 2012, and claims priority to Japanese Application No. 2012-068126 filed on Mar. 23, 2012, the entire content of both of which is incorporated herein by reference.

TECHNICAL FIELD

The present invention relates to a balloon catheter.

BACKGROUND DISCUSSION

A rapid exchange-type balloon catheter has a proximal shaft, an intermediate shaft, and a distal shaft. The guide wire opening is positioned at the boundary between the intermediate shaft and the distal shaft, and for example, a reinforcement member is arranged in the vicinity of the guide wire opening in order to prevent a kink which may be caused by a concentration of bending therein (for example, refer to JP-A-2001-95924).

A known reinforcement member has a straight shape and is arranged in a lumen in order to introduce and discharge a balloon dilation fluid. When the diameter of the reinforcement member is widened to increase rigidity thereof, a flow path for the balloon dilation fluid is narrowed, thereby exerting a negative influence on the introducing and discharging of dilation fluid. In particular, the deflation time performance, which is a contraction time of a balloon after dilation, is deteriorated.

On the other hand, if making the reinforcement member to have a tapered shape to suppress the influence on the deflation time performance, a difference in physical properties of the reinforcement member in an axial direction becomes large, and thus, the kink resistance is deteriorated.

SUMMARY

The disclosure here provides a balloon catheter in which the kink resistance and the deflation time performance can be compatible.

According to an exemplary embodiment of the disclosure, a balloon catheter is provided including a proximal shaft, a distal shaft, an intermediate shaft that is positioned between the proximal shaft and the distal shaft, a lumen that extends through the proximal shaft, the intermediate shaft, and the distal shaft and introduces and discharges a dilation fluid for a balloon, an inner tube shaft that has a guide wire opening which is arranged at the boundary between the intermediate shaft and the distal shaft and through which the lumen extends, and a reinforcement member that is arranged in the lumen so as to suppress an occurrence of a kink. The reinforcement member has a tapered proximal portion which is fixed to the proximal shaft and arranged inside the lumen positioned in the intermediate shaft, a tapered distal portion which is arranged inside the lumen positioned in the distal shaft, and a straight transition portion which is positioned between the proximal portion and the distal portion. The transition portion is aligned with the guide wire opening.

According to an exemplary embodiment of the disclosure, a reinforcement member has a substantially tapered shape and exerts a minimal influence on a flow path for a balloon dilation fluid (resistance is minimal with respect to circulation of the balloon dilation fluid), and deterioration of a deflation time performance, which is the contraction time of a balloon after dilation, is suppressed. Since the reinforcement member has a straight transition portion, a difference in physical properties thereof in an axial direction is minimal and transition of rigidity thereof is smooth, thereby having favorable kink resistance. Since the straight transition portion is aligned with a guide wire opening, for example, even if a portion of the catheter in the vicinity of the guide wire opening is bent, and a relative position between the guide wire opening (inner tube shaft) and the transition portion is changed, there is no change in the portion occupied by the transition portion in a cross section of a lumen. Thus, it is possible to minimize an influence on the deflation time performance and to secure stable deflation time performance. Therefore, it is possible to provide a balloon catheter in which the kink resistance and the deflation time performance can be compatible.

In order to minimize the difference in physical properties of the reinforcement member in the axial direction, to make a smooth transition in the rigidity thereof, and improve the kink resistance, it is preferable that in a proximal portion, a taper angle which is a tilt angle of an outer peripheral surface with respect to the axial direction of the reinforcement member changes in the middle thereof. It is preferable that the taper angle of a portion in the proximal portion which is positioned on a distal shaft side is greater than the taper angle of a portion in the proximal portion which is positioned on the proximal shaft side. It is also preferable that the taper angle of a distal portion is greater than the taper angle of the portion which is positioned in the proximal portion on the proximal shaft side, and is smaller than the taper angle of the portion which is positioned in the proximal portion on the distal shaft side.

In order to efficiently suppress the influence on the deflation time performance at the time the relative position between the guide wire opening (inner tube shaft) and a transition portion is changed, it is preferable that the center of the guide wire opening is aligned with the center of the transition portion in the axial direction of the reinforcement member. It is also preferable that a length of the transition portion in the axial direction of the reinforcement member is greater than an inner diameter of the guide wire opening.

In order to make fixing of the proximal portion of the reinforcement member easy with respect to the proximal shaft, it is preferable that a portion in the proximal portion which is fixed to the proximal shaft has a straight shape.

Other features and characteristics of the disclosure here will be apparent with reference to exemplary embodiments set forth in the following descriptions and illustrated in the accompanying drawings.

DETAILED DESCRIPTION

Hereinafter, the exemplary embodiments of the disclosure will be described with reference to the drawings.

Figure 1:
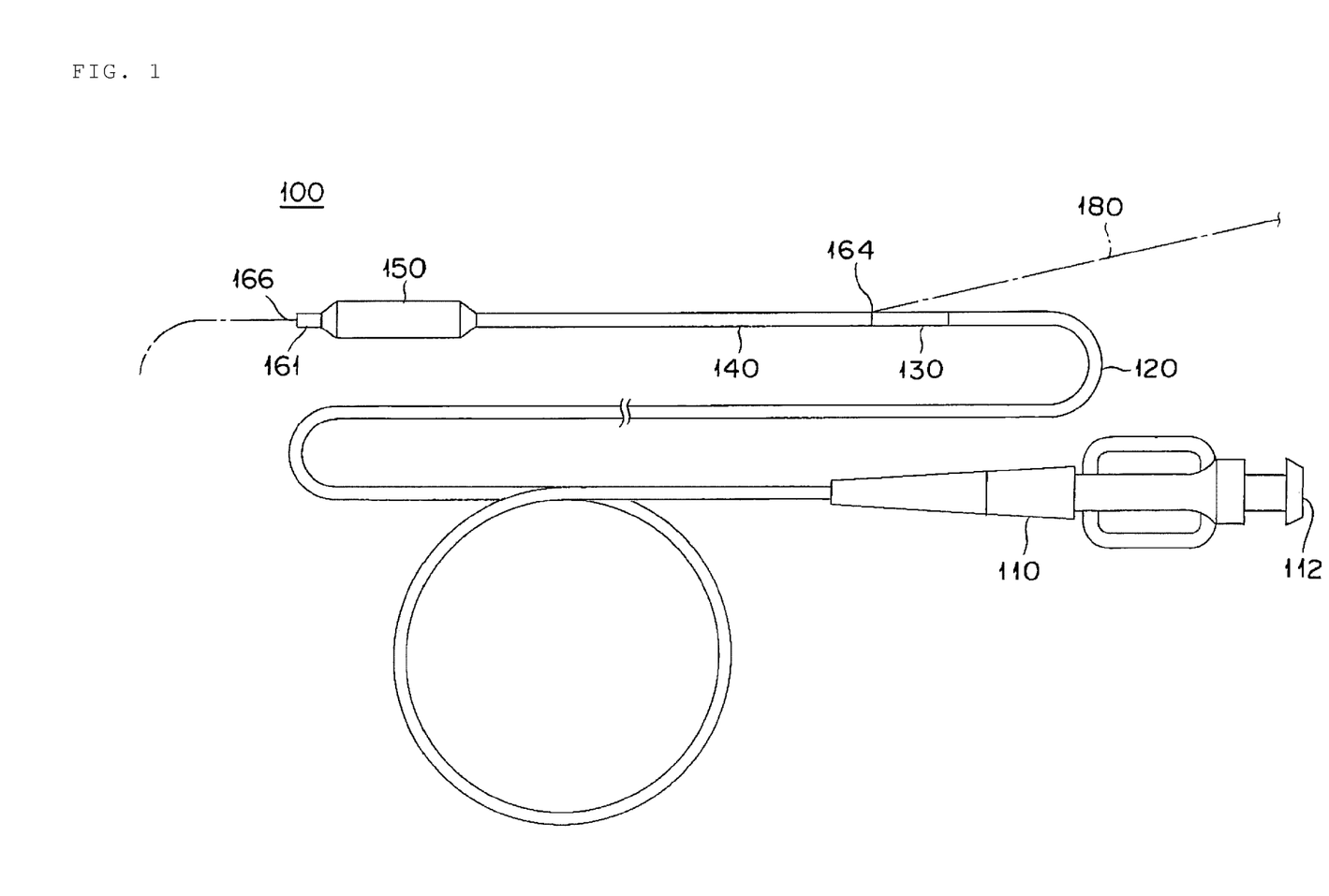
FIG. 1 is a schematic view for describing a catheter according to an exemplary embodiment of the disclosure herein.
Figure 2:
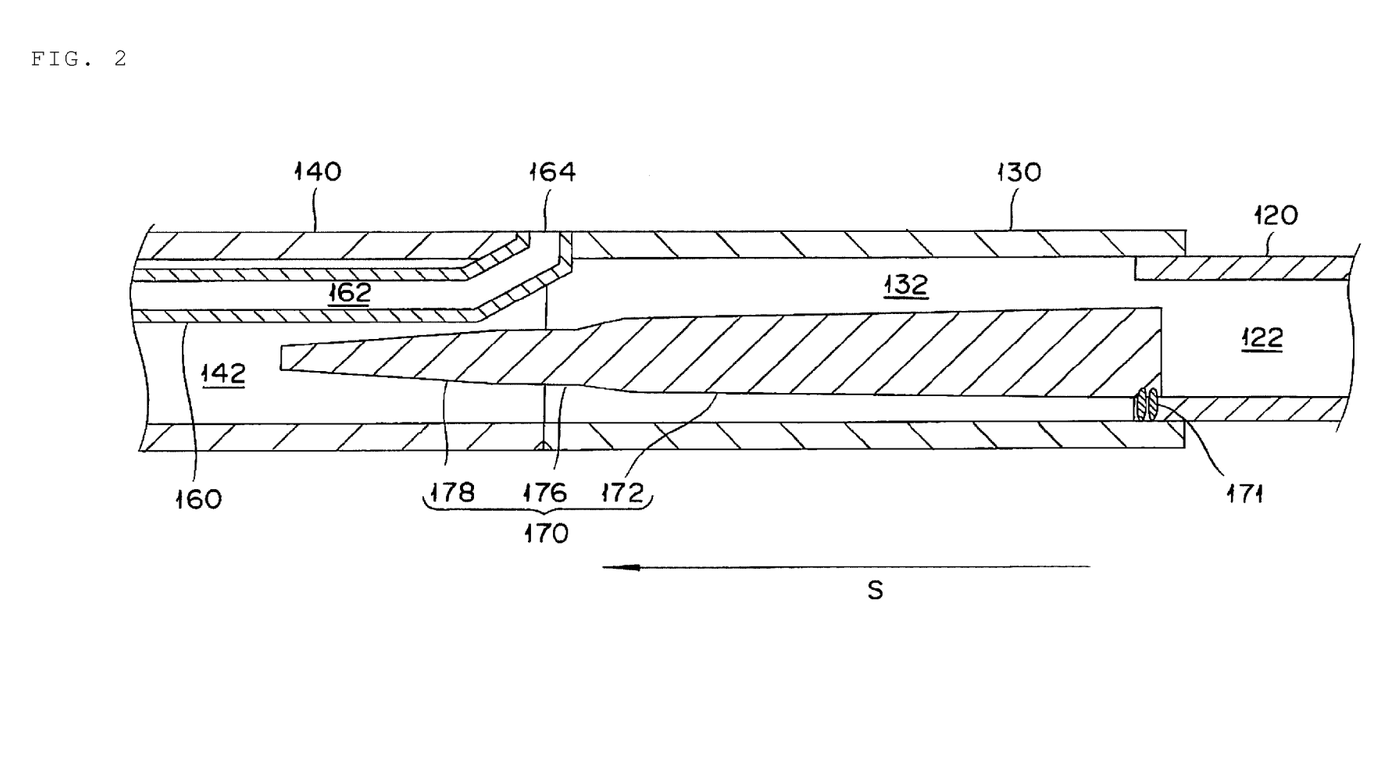
FIG. 2 is a cross-sectional view for describing the vicinity of a guide wire opening of the catheter illustrated in FIG. 1.
Figure 3:
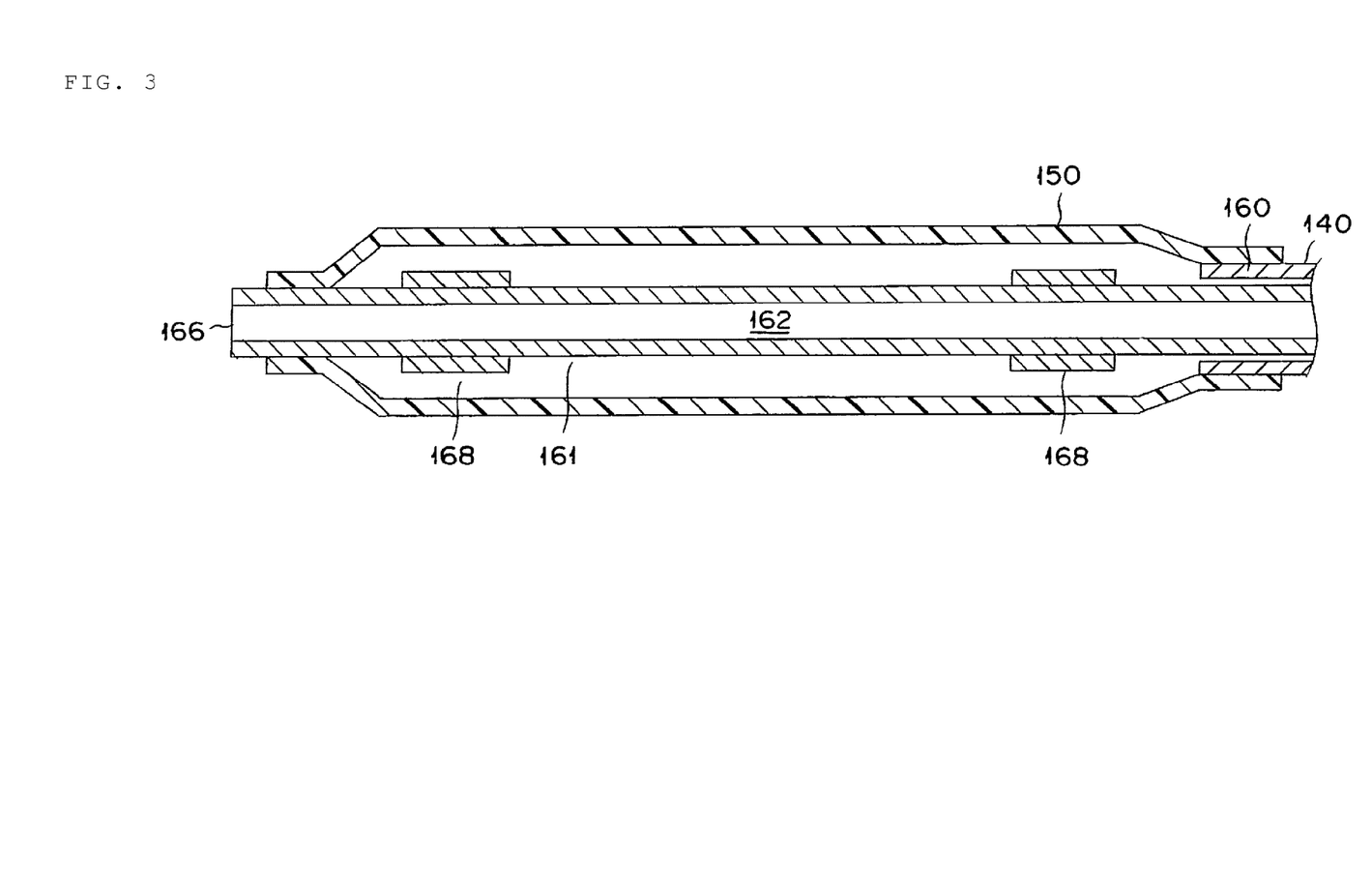
FIG. 3 is a cross-sectional view for describing the vicinity of a balloon of the catheter illustrated in FIG. 1.

FIG. 1 is a schematic view for describing a catheter according to an exemplary embodiment of the disclosure herein. FIG. 2 is a cross-sectional view for describing the vicinity of a guide wire opening of the catheter illustrated in FIG. 1. FIG. 3 is a cross-sectional view for describing the vicinity of a balloon of the catheter illustrated in FIG. 1.

A balloon catheter 100 of the exemplary embodiment of the disclosure can be applied as a treatment for sites in which a surgical operation is difficult to be performed, a treatment aiming to minimize invasive action to a human body, and an examination such as angiocardiography. The balloon catheter 100 has a hub 110, a proximal shaft 120, an intermediate shaft 130, a distal shaft 140, a balloon 150, an inner tube shaft 160, and a reinforcement member 170, which are used to guide a guide wire 180 to a target site inside a living body.

The treatment for sites in which a surgical operation is difficult to be performed is a percutaneous transluminal coronary angioplasty (PTCA) adopted for myocardial infarction or angina pectoris, for example. When the balloon catheter 100 is inserted into the vicinity of a stenosed site of the coronary artery which is the target site, the guide wire 180, protruding from a distal end of the balloon catheter 100, passes through a stenosed site to widen the stenosed site, thereby guiding the distal end of the balloon catheter 100 which follows thereafter.

As illustrated in FIG. 1, the hub 110 has an opening portion 112 in which a luer taper for connecting an auxiliary device is formed. The hub 110 is bonded to the proximal shaft 120 while maintaining a liquid-tight state. The auxiliary device is an inflator (pressure applying device) for supplying a balloon dilation fluid, for example. The balloon dilation fluid is water, physiological saline, an electrolyte solution, and the like.

The proximal shaft 120 has a tubular shape, includes a lumen 122 which communicates with the opening portion 112 of the hub 110, and is bonded to the inner tube shaft 160 while maintaining the liquid-tight state.

As illustrated in FIG. 2, the intermediate shaft 130 has a tubular shape, includes a lumen 132 which communicates with the lumen 122 of the proximal shaft 120, and is bonded to the distal shaft 140 while maintaining the liquid-tight state.

As illustrated in FIG. 3, the distal shaft 140 has a tubular shape, includes a lumen 142 which communicates with the lumen 132 of the intermediate shaft 130, and the balloon 150 is bonded thereto while maintaining the liquid-tight state.

The balloon 150 is configured to be freely dilated and communicates with the lumen 142 of the distal shaft 140. The lumen 142 of the distal shaft 140 communicates with the opening portion 112 of the hub 110 via the lumen 132 of the intermediate shaft 130 and the lumen 122 of the proximal shaft 120, and thus, the balloon dilation fluid which is introduced from the opening portion 112 of the hub 110 can reach the inside of the balloon 150.

The inner tube shaft 160 has a tubular shape, is introduced into the distal shaft 140 from a boundary between the distal shaft 140 and the intermediate shaft 130 while maintaining the liquid-tight state, and penetrates through the lumen 142 of the distal shaft 140 and the balloon 150. A distal portion 161 thereof protrudes from the balloon 150 while maintaining the liquid-tight state. The inner tube shaft 160 has a lumen 162 allowing an opening portion (guide wire opening) 164, which is positioned at the boundary between the distal shaft 140 and the intermediate shaft 130, and an opening portion 166, which is positioned on an end surface of the distal portion 161, to communicate with each other. The lumen 162 is used for inserting the guide wire 180 therethrough. The reference numeral 168 indicates a coiled contrast marker which is preferably arranged around the inner tube shaft 160. The contrast marker 168 is utilized to make the balloon 150 be easily positioned at a stenosed site through radioscopy, for example.

The reinforcement member 170 is a solid body having a substantially tapered shape relative to an axial direction S. The reinforcement member 170 is arranged in order to suppress kinks and has a proximal portion 172, a distal portion 178, and a transition portion 176.

The proximal portion 172 has a tapered shape, fixed to the proximal shaft 120, and arranged inside the lumen 132 of the intermediate shaft 130. The distal portion 178 has a tapered shape, and arranged inside the lumen 142 of the distal shaft 140. The transition portion 176 is aligned with the guide wire opening 164. The reference numeral 171 indicates a fixing (bonding) point.

The reinforcement member 170 has a substantially tapered shape and exerts a minimal influence on a flow path for the balloon dilation fluid (resistance is minimal with respect to circulation of the balloon dilation fluid), and thus, deterioration of a deflation time performance, which is the contraction time of a balloon after dilation, is suppressed. Since the reinforcement member 170 has the straight transition portion 176, a difference in physical properties thereof in the axial direction S is minimal and a transition of rigidity thereof is smooth, thereby having favorable kink resistance. The straight transition portion 176 is aligned with the guide wire opening 164. The inner space of the catheter in the vicinity of the guide wire opening 164 is narrowed due to the presence of the inner tube shaft 160. Nevertheless, even if a portion of the catheter in the vicinity of the guide wire opening 164 is bent, and a relative position between the guide wire opening 164 (inner tube shaft 160) and the straight transition portion 176 is changed, there is no change in a portion occupied by the transition portion 176 in a cross section of the lumen. Thus, it is possible to minimize an influence on the deflation time performance and to secure the stable deflation time performance. Therefore, it is possible to provide the balloon catheter 100 in which the kink resistance and the deflation time performance can be compatible.

A constituent material of the hub 110 is, for example, a thermoplastic resin such as polycarbonate, polyamide, polysulfone, polyarylate, and a methacrylate-butylene-styrene copolymer.

A constituent material of the proximal shaft 120 is a metallic material having relatively high rigidity, for example, stainless steel, a stainless steel extension alloy, an Ni—Ti alloy, brass, or aluminum. As necessary, it is possible to apply a resin material having relatively high rigidity, for example, polyimide, vinyl chloride, or polycarbonate.

The outer diameter of the proximal shaft 120 is approximately 0.3 mm to 3 mm, and is preferably 0.5 mm to 1.5 mm. The thickness of the proximal shaft 120 is approximately 10 μm to 150 μm, and is preferably 20 μm to 100 μm. The length of the proximal shaft 120 is 300 mm to 2,000 mm, and is preferably 700 mm to 1,500 mm.

A constituent material of the intermediate shaft 130 and the distal shaft 140 is, for example, a polymer material such as polyolefin, a cross-linked polyolefin, polyvinyl chloride, polyamide, a polyamide elastomer, polyester, a polyester elastomer, polyurethane, a polyurethane elastomer, a fluorine resin, and polyimide; or a mixture thereof. Polyolefin is, for example, polyethylene, polypropylene, polybutene, an ethylene-propylene copolymer, an ethylene-vinyl acetate copolymer, an ionomer, or a mixture of more than two types thereof.

The outer diameters of the distal shaft 140 and the intermediate shaft 130 are approximately 0.5 mm to 1.5 mm, and are more preferably 0.7 mm to 1.1 mm. The thicknesses of the distal shaft 140 and the intermediate shaft 130 are approximately 25 µm to 200 µm, and are more preferably 50 µm to 100 µm. The lengths of the distal shaft 140 and the intermediate shaft 130 are 300 mm to 2,000 mm, and are more preferably 300 mm to 1,500 mm.

A constituent material of the balloon 150 preferably has flexibility, for example, a polymer material such as polyolefin, a cross-linked polyolefin, polyester, a polyester elastomer, polyvinyl chloride, polyurethane, a polyurethane elastomer, polyphenylene sulfide, polyamide, a polyamide elastomer, and a fluorine resin; silicone rubber; or latex rubber. Polyester is, for example, polyethylene terephthalate. The constituent material of the balloon 150 is not limited to an embodiment of individually utilizing the above-described polymer materials. It is possible to apply a film on which the above-described polymer materials are suitably laminated.

The outer diameter of a main cylindrical portion of the balloon 150 is approximately 1.0 mm to 10 mm, and is preferably 1.0 mm to 5.0 mm, when dilated. The length of the main cylindrical portion of the balloon 150 alone is 5 mm to 50 mm, and is preferably 10 mm to 40 mm. The overall length of the balloon 150 is 10 mm to 70 mm, and is preferably 15 mm to 60 mm. A constituent material of the inner tube shaft 160 preferably has flexibility, for example, a polymer material such as polyolefin, a cross-linked polyolefin, polyvinyl chloride, polyamide, a polyamide elastomer, polyester, a polyester elastomer, polyurethane, a polyurethane elastomer, polyimide, and a fluorine resin; or a mixture thereof.

The outer diameter of the inner tube shaft 160 is approximately 0.1 mm to 1.0 mm, and is preferably 0.3 mm to 0.7 mm. The thickness of the inner tube shaft 160 is approximately 10 µm to 150 µm, and is preferably 20 µm to 100 µm. The length of the inner tube shaft 160 is 100 mm to 2,000 mm, and is preferably 200 mm to 1,500 mm.

A constituent material of the reinforcement member 170 is preferably a metallic material having favorable rigidity and workability, for example, stainless steel, a stainless steel extension alloy, or an Ni—Ti alloy.

The contrast marker 168 is configured to be made of a radiopaque material from a viewpoint in that a clear contrast image can be acquired through radioscopy. The radiopaque material is, for example, platinum, gold, tungsten, iridium, or an alloy thereof.

The reinforcement member 170 will be described in detail below.

Figure 4:
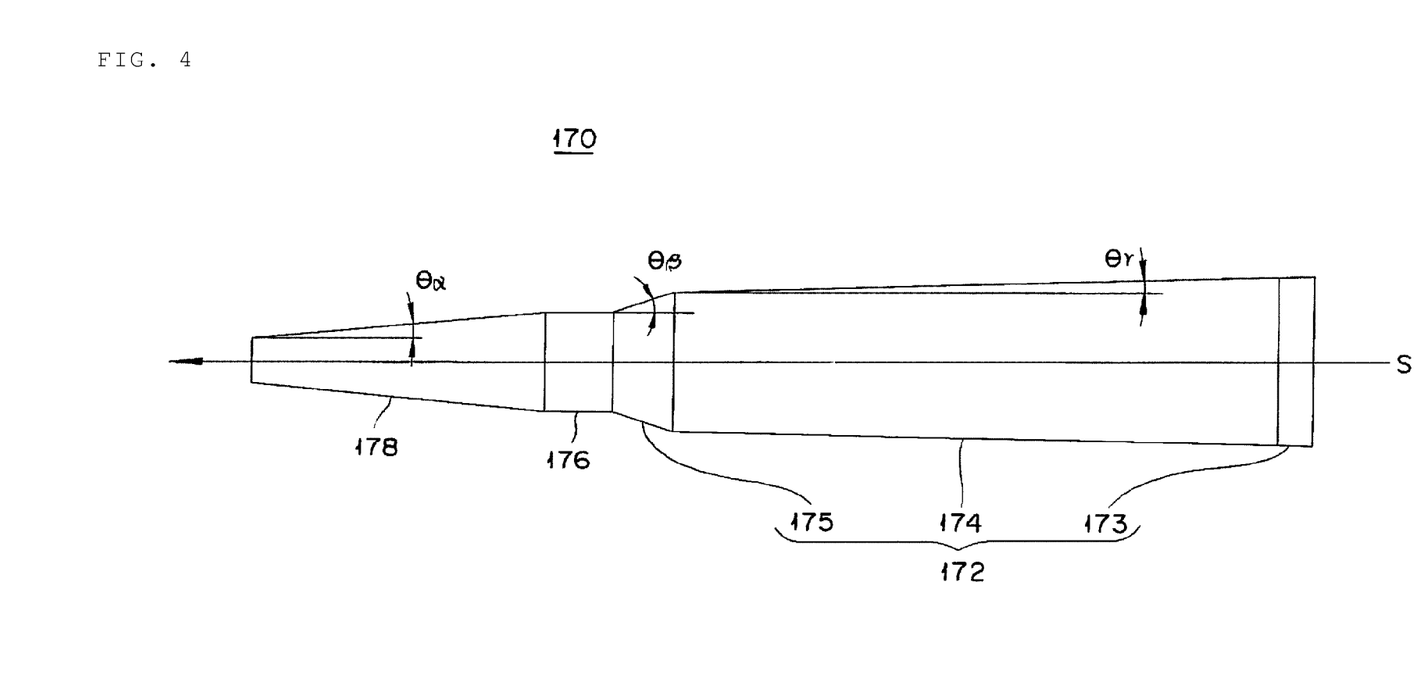
FIG. 4 is a side view for describing a shape of a reinforcement member illustrated in FIG. 2.

FIG. 4 is a side view for describing a shape of the reinforcement member illustrated in FIG. 2.

For the purposes of explanation, it is assumed that the outer diameter and the inner diameter of the proximal shaft 120 are respectively 0.64 mm and 0.46 mm; the outer diameter, the inner diameter, and the length of the intermediate shaft 130 are respectively 0.85 mm, 0.67 mm, and 150 mm; the outer diameter and the inner diameter of the distal shaft 140 are respectively 0.88 mm and 0.76 mm; the outer diameter of the inner tube shaft 160 is 0.56 mm; and the inner diameter (inner diameter of guide wire opening 164) of the inner tube shaft 160 is 0.41 mm.

The proximal portion 172 of the reinforcement member 170 is configured to include a base portion 173, a first tapered portion 174, and a second tapered portion 175.

The base portion 173 is a portion to be fixed (bonded) to the proximal shaft 120, and is caused to have a straight shape so as to be easily fixed thereto. For example, the length and the outer diameter of the base portion 173 are respectively 5.0 mm and 0.34 mm. A fixing method is not particularly limited, and welding is applied, for example.

The first tapered portion 174 is positioned on the base portion 173 side (proximal shaft 120 side), and the second tapered portion 175 is positioned on the transition portion 176 side (distal shaft 140 side). A taper angle $\theta_\beta$ of the first tapered portion 174 differs from a taper angle $\theta_\gamma$ of the second tapered portion 175, and the taper angle $\theta_\beta$ is greater than the taper angle $\theta_\gamma$. In other words, the taper angles of the tapered portions 174 and 175 of the proximal portion 172 change in the middle thereof. Accordingly, the difference in physical properties of the reinforcement member 170 in the axial direction S is minimized and the transition of rigidity thereof is smooth, thereby improving the kink resistance. For example, the length, the outer diameter at the boundary with respect to the base portion 173, and the taper angle $\theta_\gamma$ of the first tapered portion 174 are respectively 95.0 mm, 0.34 mm, and 0.02 degrees. The length, the outer diameter at the boundary with respect to the transition portion 176, and the taper angle $\theta_\beta$ of the second tapered portion 175 are respectively 10.0 mm, 0.28 mm, and 0.23 degrees.

The length of the transition portion 176 is greater than the inner diameter of the guide wire opening 164, and the center of the guide wire opening 164 is aligned with the center of the transition portion 176 regarding the axial direction S. Accordingly, at the time the relative position between the guide wire opening 164 (inner tube shaft 160) and the transition portion 176 is changed, it is possible to efficiently suppress the influence on deflation time performance. For example, the length of the transition portion 176 is 10.0 mm, and in this case, changes of ±5.0 mm at the maximum are absorbed.

A taper angle $\theta_\alpha$ of the distal portion 178 is greater than the taper angle $\theta_\gamma$ of the first tapered portion 174 and smaller than the taper angle $\theta_\beta$ of the second tapered portion 175 of the proximal portion 172. Accordingly, the difference in physical properties of the reinforcement member 170 in the axial direction S is minimized and the transition of rigidity thereof is smooth, thereby improving the kink resistance. For example, the length, the outer diameter on an end surface of the distal end, the outer diameter at the boundary with respect to the transition portion 176, and the taper angle $\theta_\alpha$ of the distal portion 178 are respectively 45.0 mm, 0.10 mm, 0.20 mm, and 0.06 degrees.

Figure 5:
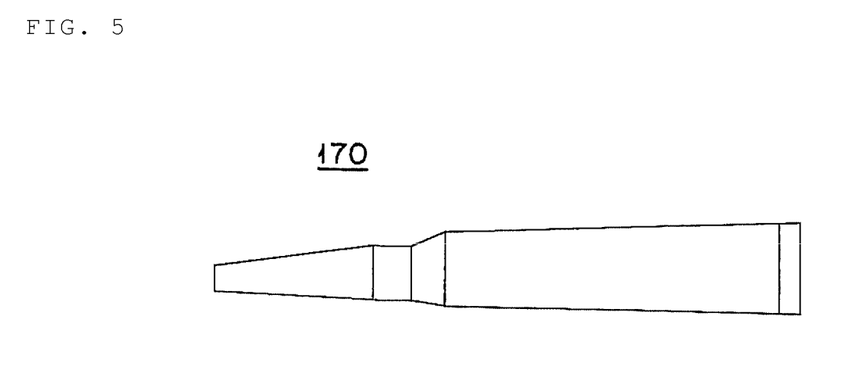
FIG. 5 is a side view for describing Modification Example 1 of the catheter according to the exemplary embodiment of the disclosure herein.
Figure 6:
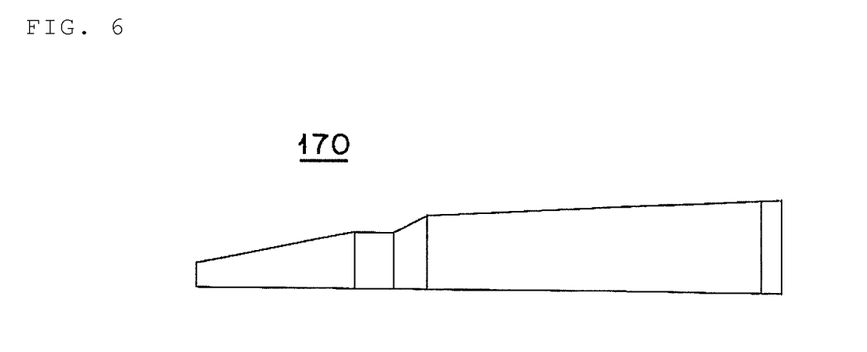
FIG. 6 is a side view for describing Modification Example 2 of the catheter according to the exemplary embodiment of the disclosure herein.
Figure 7:
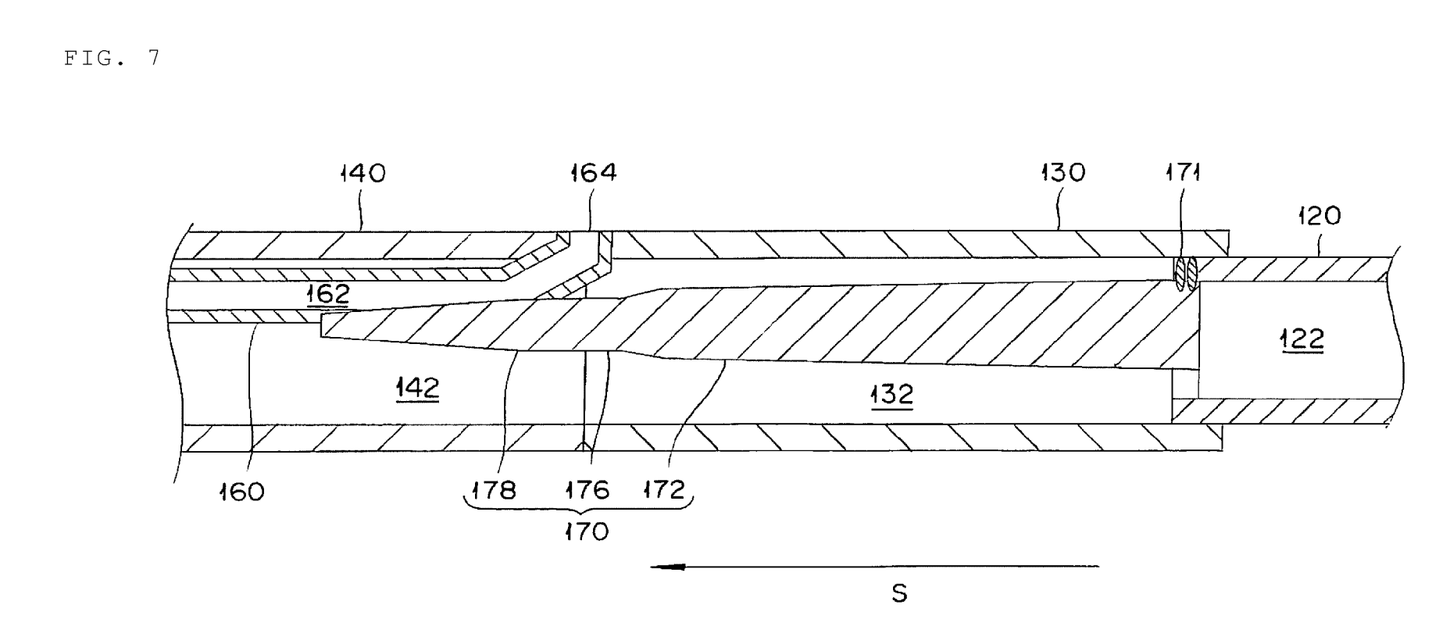
FIG. 7 is a cross-sectional view for describing Modification Example 3 of the catheter according to the exemplary embodiment of the disclosure herein.

Modification Examples 1 to 3 of a catheter according to further exemplary embodiments of the disclosure will be described.

FIGS. 5 and 6 are side views for describing Modification Examples 1 and 2.

The reinforcement member 170 is not limited to a symmetric shape regarding the axial direction S, and can have a distorted tapered shape. For example, it is possible to minimize the taper angle on a side to be fixed to the proximal shaft 120 (refer to FIG. 5) or to have a plane shape (refer to FIG. 6). In this case, it is preferable that the taper angle is caused to be greater in portions other than the portion in which the taper angle is minimized or the portion which is caused to have the plane shape in order to secure a shape (taper angle) of the reinforcement member 170 in its entirety.

FIG. 7 is a cross-sectional view for describing Modification Example 3.

Fixing of the proximal portion 172 (base portion 173) of the reinforcement member 170 with respect to the proximal shaft 120 is not limited to the exemplary embodiment of applying a portion which is positioned on a side opposite to the side where the guide wire opening 164 is positioned. For example, it is possible to utilize a portion on a side where the guide wire opening 164 is positioned to be fixed to the proximal shaft 120.

As described above, in the exemplary embodiment of Modification Example 3, the reinforcement member has a substantially tapered shape and exerts a minimal influence on the flow path for the balloon dilation fluid (resistance is minimal with respect to circulation of the balloon dilation fluid), and the deflation time performance which is a contraction time of a balloon after dilation is suppressed from being deteriorated. Since the reinforcement member has the straight transition portion, the difference in physical properties of the reinforcement member in the axial direction is minimal and the transition of rigidity thereof is smooth, thereby having favorable kink resistance. Since the straight transition portion is aligned with the guide wire opening, for example, even if the portion of the catheter in the vicinity of the guide wire opening may be bent, and the relative position between the guide wire opening (inner tube shaft) and the straight transition portion is changed, there is no change in the portion occupied by the transition portion in a cross section of the lumen. Thus, it is possible to minimize the influence on the deflation time performance and to secure the stable deflation time performance. Therefore, it is possible to provide a balloon catheter in which the kink resistance and the deflation time performance can be compatible.

The disclosure herein is not limited to the above-described exemplary embodiments, and various changes and modifications can be within the scope of the claims. For example, the present invention can be applied to a stent delivery. The balloon and the distal shaft can be coated with a hydrophilic polymer. In this case, a coefficient of friction at the time of coming into contact with blood or physiological saline is reduced and lubricity (sliding property) is improved, and thus, an insertion property with respect to a body cavity becomes favorable. The hydrophilic polymer is, for example, a cellulose-based polymeric material such as hydroxypropyl cellulose, a polyethylene oxide-based polymeric material such as polyethylene glycol, a maleic anhydride-based polymeric material such as a maleic anhydride copolymer such as a methyl vinyl ether-maleic anhydride copolymer, an acrylamide-based polymeric material such as a dimethyl acrylamide-glycidyl methacrylate copolymer, or water-soluble nylon.

The detailed description above describes a balloon catheter. The invention is not limited, however, to the precise exemplary embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
   a proximal shaft;
   a distal shaft;
   an intermediate shaft that is positioned between the proximal shaft and the distal shaft;
   a lumen that extends through the proximal shaft, the intermediate shaft, and the distal shaft and is configured to introduce and discharge a dilation fluid for a balloon;
   an inner tube shaft that extends through the lumen and has a guide wire opening arranged at a boundary between the intermediate shaft and the distal shaft; and
   a reinforcement member arranged in the lumen so as to suppress an occurrence of a kink in the balloon catheter;
   wherein the reinforcement member has a tapered proximal portion which is fixed to the proximal shaft and arranged inside the lumen positioned in the intermediate shaft, a tapered distal portion which is arranged inside the lumen positioned in the distal shaft, and a straight transition portion which is positioned between the proximal portion and the distal portion, the straight transition portion possessing an outer diameter that is constant; and
   wherein the transition portion is aligned with the guide wire opening.

2. The balloon catheter according to claim 1, wherein a taper angle of the proximal portion changes in the middle thereof, the taper angle being a tilt angle of an outer peripheral surface with respect to an axial direction of the reinforcement member.

3. The balloon catheter according to claim 2, wherein the taper angle of a portion which is positioned in the proximal portion on the distal shaft side is greater than the taper angle of a portion which is positioned in the proximal portion on the proximal shaft side.

4. The balloon catheter according to claim 3, wherein the taper angle of the distal portion is greater than the taper angle of the portion in the proximal portion which is positioned on the proximal shaft side, and is smaller than the taper angle of the portion in the proximal portion which is positioned on the distal shaft side.

5. The balloon catheter according to claim 1, wherein a center of the guide wire opening is aligned with a center of the transition portion relative to an axial direction of the reinforcement member.

6. The balloon catheter according to claim 1, wherein a length of the transition portion relative to an axial direction of the reinforcement member is greater than an inner diameter of the guide wire opening.

7. The balloon catheter according to claim 1, wherein a portion of the proximal portion which is fixed to the proximal shaft has a straight shape.

8. The balloon catheter according to claim 1, further comprising a balloon, wherein a distal portion of the inner tube shaft protrudes from the balloon.

9. The balloon catheter according to claim 1, wherein the reinforcement member is formed from a metallic material.

10. The balloon catheter according to claim 1, wherein a taper angle of the proximal portion changes relative to an axial direction thereof, the taper angle being a tilt angle of an outer peripheral surface with respect to an axial direction of the reinforcement member.

11. The balloon catheter according to claim 10, wherein the taper angle is asymmetric.

12. The balloon catheter according to claim 1, wherein the tapered proximal portion of the reinforcement member includes a base portion, a first tapered portion and a second tapered portion.

13. The balloon catheter according to claim 12, wherein the base portion is fixed to the proximal shaft.

14. The balloon catheter according to claim 13, wherein the first tapered portion is positioned distal to the base portion and the second tapered portion is positioned distal to the first tapered portion and proximal to the straight transition portion.

15. The balloon catheter according to claim 14, wherein a first taper angle of the first tapered portion differs from a second taper angle of the second tapered portion, the taper angle being a tilt angle of an outer peripheral surface with respect to an axial direction of the reinforcement member.

16. The balloon catheter according to claim 14, wherein the first taper angle is greater than the second taper angle.

17. The balloon catheter according to claim 16, wherein a third taper angle of the tapered distal portion is greater than the first taper angle of the first tapered portion and smaller than the second taper angle of the second tapered portion.

* * * * *